United States Patent

Tanaka et al.

[11] Patent Number: 6,017,929
[45] Date of Patent: Jan. 25, 2000

[54] CHOLINESTERASE ACTIVATOR

[75] Inventors: Yoshiaki Tanaka; Naomi Kobayashi; Naoki Nakata; Itaru Yamaguchi; Tadashi Mori, all of Konan-machi, Japan

[73] Assignee: Zeria Pharmaceutical Co., Ltd., Tokyo, Japan

[21] Appl. No.: 08/687,446

[22] PCT Filed: Feb. 17, 1995

[86] PCT No.: PCT/JP95/00229

§ 371 Date: Aug. 15, 1996

§ 102(e) Date: Aug. 15, 1996

[87] PCT Pub. No.: WO95/22326

PCT Pub. Date: Aug. 24, 1995

[30] Foreign Application Priority Data

Feb. 17, 1994 [JP] Japan .................................... 6-041714

[51] Int. Cl.[7] .......................... A01N 43/40; A61K 31/445
[52] U.S. Cl. ................... 514/315; 514/231.2; 514/237.5; 514/227.5; 514/319
[58] Field of Search .................................... 514/315, 319, 514/231.2, 237.5, 227.5

[56] References Cited

U.S. PATENT DOCUMENTS 5,120,843  6/1992  McCall et al. ........................... 544/123

FOREIGN PATENT DOCUMENTS

WO 91/18891  12/1991  WIPO .
WO 95/01352  1/1995  WIPO .

OTHER PUBLICATIONS

Scopes et al., "New k–Receptor Agonists Based upon a 2-[(Alkylamino)methyl]piperidine Nucleus", J. Med. Chem 35 (No. 3), pp. 490–451, 1992.

*Primary Examiner*—William R. A. Jarvis
*Assistant Examiner*—Dwayne C. Jones
*Attorney, Agent, or Firm*—Oblon, Spivak, McClelland, Maier & Neustadt, P.C.

[57] ABSTRACT

The invention relates to a cholinesterase activator comprising, as an active ingredient, a compound represented by the following general formula (I):

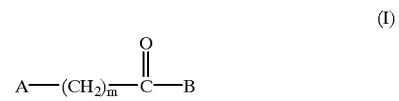

wherein A means a group such as a phenyl group or indanyl group, B denotes a group such as a prolyl group or thioprolyl group, and m stands for an integer of 0–5.

The cholinesterase activator according to the invention has a strongly activating action on cholinesterase, in particular, a selectively activating action on peripheral cholinesterase and is also high in safety. It is hence useful as an agent for preventing and treating the side effects of central cholinesterase inhibitors, in particular, hepatopathy, and an agent for preventing and treating the side effects of various medicines manifested on the basis of a cholinesterase-inhibiting action.

4 Claims, No Drawings

CHOLINESTERASE ACTIVATOR

TECHNICAL FIELD

The present invention relates to a cholinesterase activator, and more particularly to a cholinesterase activator which selectively enhances peripheral cholinesterase activities and is high in safety.

BACKGROUND ART

Cholinesterase is an enzyme that is widely distributed in a living body and hydrolyzes choline esters such as acetylcholine.

As the cholinesterase, there have heretofore been known two kinds of cholinesterase, i.e., specific (true) cholinesterase that exists in a brain, nervous tissue such as an autonomic nerve and a neuromuscles junction, an erythrocyte membrane, and the like, and nonspecific (pseudo) cholinesterase that exists in a serum, the pancreas and the like.

These kinds of cholinesterase are inhibited not only by cholinesterase inhibitors such as neostigmine but also by various medicines, in particular, carcinostatics, organic phosphorus agents and the like. The reduction in cholinesterase activities is considered to form the main cause that the side effects of various medicines are manifested. It is further known that cholinesterase activities are reduced even by hepatopathy.

For example, irinotecan hydrochloride, which is in use as a carcinostatic, is recognized to manifest grave diarrhea as a side effect. The diarrhea is manifested on the basis of a cholinesterase-inhibiting action due to administration of irinotecan hydrochloride.

Besides, 1,2,3,4-tetrahydro-9-acridinamine (hereinafter referred to as "THA") of a cholinesterase inhibitor, which has been used as a remedy for an Alzheimer's disease in recent years, inhibits not only central cholinesterase but also peripheral cholinesterase and is hence recognized to manifest side effects such as sialorrhea, nausea, diarrhea sweating and hepatopathy.

On the other hand, when the central cholinesterase is activated, the amount of acetylcholine in a brain is decreased, so that the diseased condition of a patient suffering from a Parkinson disease, senile dementia or the like is considered to be worsened.

Accordingly, it is necessary to administer an agent, which can selectively activate the peripheral cholinesterase, for the side effects of various medicines manifested on the basis of their cholinesterase-inhibiting action. However, any agent which can selectively activate central or peripheral cholinesterase has not been yet present, and there is hence a demand for development of a novel cholinesterase activator having such a selectively activating action.

The present inventors have carried out an extensive investigation with a view toward solving the above problem. As a result, it has been surprisingly found that a compound represented by the general formula (I) has a strongly activating action on cholinesterase, and such a activating action selectively works on peripheral cholinesterase, thus leading to completion of the present invention.

DISCLOSURE OF THE INVENTION

The present invention provides a cholinesterase activator comprising, as an active ingredient, a compound represented by the following general formula (I):

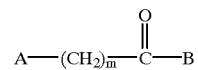

wherein A means a group represented by the following general formula

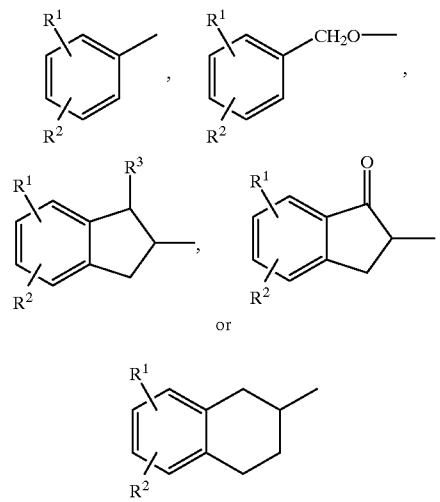

in which $R^1$ and $R^2$ are identical with or different from each other and denote individually a hydrogen atom, alkyl group, alkoxyl group, nitro group, amino group or halogen atom, $R^3$ means a hydrogen atom or a hydroxyl group, B denotes a group represented by the following formula

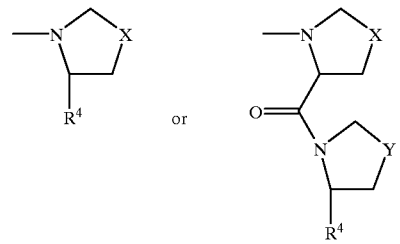

in which $R^4$ denotes a hydrogen atom, formyl group, cyano group, dialkoxymethyl group, carboxyl group, alkoxycarbonyl group or hydroxymethyl group, X means a methylene group, ethylene group, oxygen atom, sulfur atom, sulfinyl group, sulfonyl group or —$CH_2$—S—, and Y represents a methylene group, ethylene group, —$CH_2$—S—, sulfur atom, sulfinyl group or sulfonyl group, and m stands for an integer of 0–5.

The present invention also provides an agent for preventing and treating a disease manifested on the basis of the reduction of cholinesterase activities, which comprises, as an active ingredient, the compound represented by the general formula (I).

The present invention further provides use of the compound represented by the general formula (I) for a cholinesterase activator.

The present invention still further provides use of the compound represented by the general formula (I) for an agent for preventing and treating a disease manifested on the basis of the reduction of cholinesterase activities.

The present invention yet still further provides a method for treating a disease manifested on the basis of the reduction of cholinesterase activities, which comprises administering an effective amount of the compound represented by the general formula (I).

BEST MODE FOR CARRYING OUT THE INVENTION

The compounds represented by the general formula (I) are known compounds disclosed as prolyl endopeptidase inhibitors in Japanese Patent Application Laid-Open Nos. 148467/1987, 201877/1987, 124818/1990 and 160772/1990, and also Japanese Patent Application Laid-Open Nos. 250370/1989, 262557/1990, 207070/1990, 151323/1991, 9367/1992 and 261151/1992 and International Publication No. WO91/18877 which were applied for patent by the present applicant, and may be prepared in accordance with the methods described therein.

In the general formula (I), the alkyl groups indicated by $R^1$ and $R^2$ include linear or branched alkyl groups having 1–6 carbon atoms with linear or branched alkyl groups having 1–4 carbon atoms being particularly preferred. Specific examples of the alkyl groups include methyl, ethyl, n-propyl, isopropyl, n-butyl, isobutyl, sec-butyl and tert-butyl groups. The alkoxyl groups include linear or branched alkoxyl groups having 1–6 carbon atoms with linear or branched alkoxyl groups having 1–4 carbon atoms being particularly preferred. Specific examples of the alkoxyl groups include methoxyl, ethoxyl, n-propoxyl, isopropoxyl, n-butoxyl, isobutoxyl, sec-butoxyl and tert-butoxyl groups.

The halogen atoms include fluorine, chlorine, bromine and iodine atoms.

Examples of "alkoxy" in the dialkoxymethyl group and the alkoxycarbonyl group indicated by $R^4$ include the same groups as the alkoxyl groups mentioned above.

The compounds (I) useful in the practice of the present invention may have 1–3 asymmetric carbon atoms in some cases. In the present invention, however, the configuration of a substituent on each of the asymmetric carbon atoms may be either R or S, and a mixture thereof may be permissible.

Since the compounds (I) have an excellent cholinesterase-activating action as described below and are high in safety, they are useful as agents for preventing and treating various diseases caused by the reduction of cholinesterase activities. In particular, they selectively activate peripheral cholinesterase and hence are also useful as agents for preventing and treating the side effects of medicines, in which cholinesterase inhibition is considered the main cause that the side effects are manifested. Further, the compounds (I) are useful as agents for preventing and treating the side effects of central cholinesterase inhibitors because they do not affect cholinesterase activities in brain parenchyma.

Examples of the disease manifested on the basis of the reduction of cholinesterase activities, for which the present invention is intended, include side effects caused by various cholinesterase inhibitors, for example, diarrhea, sialorrhea, nausea and hepatopathy, and besides Parkinson disease, senile dementia, etc.

A cholinesterase activator and an agent for preventing and treating a disease manifested on the basis of the reduction of cholinesterase activities, which each comprises, as an active ingredient, the compound (I) according to the present invention, can be formulated into a preparation for oral administration or parenteral administration by incorporating pharmaceutically permissible additives. The preparation for oral administration can be provided in the form of tablets, powders, granules and capsules by suitably combining the above compound with proper additives such as, for example, excipients such as lactose, mannite, corn starch and crystalline cellulose, binders such as cellulose derivatives, gum arabic and gelatin, disintegrators such as calcium carboxymethylcellulose, and lubricants such as talc and magnesium stearate. These solid preparations can be provided as enteric coated preparations by using a coating base such as hydroxypropylmethylcellulose phthalate, hydroxypropylmethylcellulose acetate succinate, cellulose acetate phthalate or a methacrylate copolymers. The preparation for parenteral administration can be provided in the form of solutions for injection by suitably combining the compound with water, ethanol, glycerol, conventional surfactants and the like, or in the form of suppositories by using a base for suppository.

The dose of such a preparation varies according to the age, weight and diseased condition of a patient to be dosed, therapeutic effect, administration method and administration period. In the case of oral administration, however, it is preferable to dose the preparation in a proportion of generally 0.1–2,000 mg/day, particularly 1–600 mg/day at once or in 2–3 installments.

EXAMPLES

The present invention will hereinafter be described in detail by the following Examples. However, the present invention is not limited by these examples.

Synthetic Example 1

N-(4-Phenylbutanoyl)-L-thioprolylthiazolidine (Compound 1)

Dissolved in 100 ml of 1N sodium hydroxide were 6.65 g of L-thioproline, and 50 ml of water were further added to the solution. A solution of 9.10 g of 4-phenylbutanoyl chloride in 50 ml of benzene was added dropwise to the solution under stirring. Thereafter, 50 ml of 1N sodium hydroxide were further added, and the mixture was stirred for 24 hours. A benzene layer was removed, and a water layer was washed twice with 70 ml of ether. After 7% hydrochloric acid was further added to the water layer to acidify it, the water layer was extracted three times with 70 ml of ethyl acetate. The resulting extract was dried over anhydrous sodium sulfate. Ethyl acetate was distilled off, and the resultant oily residue was subjected to column chromatography on silica gel, thereby obtaining 11.4 g of N-(4-phenylbutanoyl)-L-thioproline as colorless crystals from a chloroform-methanol fraction.

To 20 ml of methylene chloride, 1.4 g of the thus-obtained N-(4-phenylbutanoyl)-L-thioproline were added together with 445 mg of thiazolidine and 1.05 g of 1-ethyl-3-(3-dimethylaminopropyl)carbodiimide hydrochloride [WSC (Water Soluble Carbodiimide).HCl], and the mixture was stirred for 24 hours. The resultant liquid reaction mixture was washed with 1N hydrochloric acid, saturated saline, a saturated aqueous solution of sodium bicarbonate and saturated saline in that order and dried over anhydrous sodium sulfate. Methylene chloride was distilled off, and the resultant oily residue was subjected to column chromatography on silica gel, thereby obtaining 833 mg of the intended N-(4-phenyl-butanoyl)-L-thioprolylthiazolidine as colorless crystals from a chloroform-methanol fraction.

mp: 80–82° C., $[\alpha]_D^{22}$ –93.0° (C=1, MeOH)

IR (KBr) cm$^{-1}$: 2940, 1635, 1420, 1410, 1340, 1265, 740, 700.

Synthetic Examples 2–17

The following compounds were synthesized in the same manner as in Synthetic Example 1.

N-(4-Phenylbutanoyl)-L-prolylthiazolidine (Compound 2)

mp: 53–55° C., $[\alpha]_D^{22}$ –24° (C=1, MeOH)

IR (KBr) cm$^{-1}$: 2950, 1635, 1435, 1350, 1320, 1265, 740, 700.

N-(4-Phenylbutanoyl)-L-thioprolylpyrrolidine (Compound 3)
mp: 67–70° C., $[\alpha]_D^{22}$ –105.6° (C=1, MeOH)
IR (KBr) cm$^{-1}$: 2880, 1635, 1445, 1410, 1290, 1160.
N-(4-Phenylbutanoyl)-D-prolylthiazolidine (Compound 4)
$[\alpha]_D^{22}$ +24° (C=1, MeOH).
N-(4-Phenylbutanoyl)-L-prolylpyrrolidine (Compound 5)
IR (KBr) cm$^{-1}$: 2970, 2870, 1640, 1430, 1320, 740.
N-(4-Phenylbutanoyl)-L-prolylprolinal (Compound 6)
IR (KBr) cm$^{-1}$: 2970, 2670, 1730, 1630, 1440, 1320, 740.
N-Benzyloxycarbonyl-prolylprolinal (Compound 7)
mp: 99–101° C.
N-Benzyloxycarbonyl-prolylpiperidine (Compound 8)
mp: 90–92° C.
N-Benzyloxycarbonyl-prolylpyrrolidine (Compound 9)
mp: 129–131° C.
N-Benzyloxycarbonyl-thioprolylpyrrolidine (Compound 10)
mp: 88–90° C.
N-Benzyloxycarbonyl-prolylthiazolidine (Compound 11)
mp: 112–114° C.
N-Benzyloxycarbonyl-thioprolylthiazolidine (Compound 12)
mp: 73–75° C.
N-Benzyloxycarbonyl-thioprolylthioproline methyl ester (Compound 13)
mp: 102–104° C.
N-Benzyloxycarbonyl-prolylthioproline (Compound 14)
mp: 183–185° C. (decomposed).
2-Carboxy-1-(N-benzyloxycarbonyl)prolylpiperidine (Compound 15)
mp: 66–69° C.
N-Benzyloxycarbonyl-thioprolylthioproline (Compound 16)
mp: 188–189° C.
N-Benzyloxycarbonyl-L-thioprolyl-L-thioprolinal dimethyl acetal (Compound 17)
IR (KBr) cm$^{-1}$: 2990, 2930, 1645, 1410, 1350, 1110, 1075.

Synthetic Example 18

3-(2-Indanylacetyl)-L-thioproline ethyl ester (Compound 18)

While chilling with ice water, 1.4 g of 2-indanyl-acetic acid and 1.9 g of WSC.HCl were added to 15 ml of methylene chloride, and the mixture was stirred at room temperature for 5 minutes. Then, 1.3 g of L-thioproline ethyl ester dissolved in 10 ml of methylene chloride were added at room temperature, and the mixture was stirred further for 5 hours. The resultant liquid reaction mixture was washed with water, diluted hydrochloric acid and a saturated aqueous solution of sodium bicarbonate in that order. After an organic layer was dried over anhydrous magnesium sulfate, the solvent was distilled off under reduced pressure, and the resultant residue was subjected to column chromatography on silica gel, thereby obtaining 1.45 g (57%) of 3-(2-indanylacetyl)-L-thioproline ethyl ester in the form of colorless oil.

IR (neat) cm$^{-1}$: 2940, 1735, 1650, 1400.

Synthetic Examples 19–70

The following compounds were synthesized in the same manner as in Synthetic Example 18.
3-(2-Indanylacetyl)-L-thioproline (Compound 19)
mp: 152–154° C.
IR (KBr) cm$^{-1}$: 2900, 1720, 1600, 1430, 1220, 730.
1-(2-Indanylacetyl)-L-proline methyl ester (Compound 20)
mp: 71–73° C.
IR (KBr) cm$^{-1}$: 3070–2850, 1745, 1645, 1430, 1195, 1170, 745.
1-(2-Indanylacetyl)-L-proline (Compound 21)
mp: 97–99° C.
IR (KBr) cm$^{-1}$: 3460–2500, 1730, 1600, 1440, 1315, 1180, 740.
Methyl 4-(2-indanylacetyl)-DL-1,4-thiazane-3-carboxylate (Compound 22)
mp: 77–79° C.
IR (KBr) cm$^{-1}$: 2940, 1741, 1653, 1417, 1337, 1229, 1194, 1012.
4-(2-Indanylacetyl)-DL-1,4-thiazane-3-carboxylic acid (Compound 23)
mp: 65–682° C.
IR (KBr) cm$^{-1}$: 2910, 1725, 1600, 1420, 1310, 1285, 1180.
Ethyl 4-(2-indanylacetyl)-DL-1,4-thiazane-3-carboxylate (Compound 24)
mp: 82–840° C.
IR (KBr) cm$^{-1}$: 2925, 1735, 1645, 1410, 1365, 1285, 1225, 1185, 1025.
Ethyl 1-(2-indanylacetyl)-DL-piperidine-2-carboxylate (Compound 25)
IR (neat) cm$^{-1}$: 2950, 1730, 1640, 1420, 740.
1-(2-Indanylacetyl)-DL-piperidine-2-carboxylic acid (Compound 26)
mp: 147–148° C.
IR (KBr) cm$^{-1}$: 2950, 1740, 1590, 750.
1-(2-Indanylacetyl)-L-piperidine-2-carboxylic acid (Compound 27)
mp: 152–153° C.
IR (KBr) cm$^{-1}$: 2950, 1740, 1590, 750.
1-(2-Indanylacetyl)-D-piperidine-2-carboxylic acid (Compound 28)
mp: 152–153° C.
IR (KBr) cm$^{-1}$: 2950, 1740, 1590, 750.
1-(1,2,3,4-Tetrahydronaphthalen-2-yl-carbonyl)-L-proline methyl ester (Compound 29)
IR (neat) cm$^{-1}$: 3050–2840, 1740, 1640, 1430, 1195, 1170, 745.
1-(1,2,3,4-Tetrahydronaphthalen-2-yl-carbonyl)-L-proline (Compound 30)
IR (neat) cm$^{-1}$: 3420–2570, 1735, 1600, 1450, 1185, 740.
1-(1,2,3,4-Tetrahydronaphthalen-2-yl-acetyl)-L-proline (Compound 31)
mp: 112–134° C.
IR (KBr) cm$^{-1}$: 3200–2450, 1745, 1710, 1605, 1450, 760, 750.
3-(1,2,3,4-Tetrahydronaphthalen-2-yl-acetyl)-L-thioproline ethyl ester (Compound 32)
IR (neat) cm$^{-1}$: 2925, 1745, 1645, 1400, 740.
3-(1,2,3,4-Tetrahydronaphthalen-2-yl-acetyl)-L-thioproline (Compound 33)
mp: 120–125° C.
IR (KBr) cm$^{-1}$: 2925, 1725, 1580, 1450, 730.
1-(6-Methoxy-1,2,3,4-tetrahydronaphthalen-2-yl-acetyl)-L-proline methyl ester (Compound 34)
IR (neat) cm$^{-1}$: 3000–2825, 1735, 1630, 1165, 1030.
1-(6-Methoxy-1,2,3,4-tetrahydronaphthalen-2-yl-acetyl)-L-proline (Compound 35)
mp: 144–149° C.
IR (KBr) cm$^{-1}$: 3000–2825, 1700, 1685, 1230.
3-(6-Methoxy-1,2,3,4-tetrahydronaphthalen-2-yl-acetyl)-L-thioproline ethyl ester (Compound 36)
IR (neat) cm$^{-1}$: 2910, 1740, 1650, 1500, 1400, 750.
3-(6-Methoxy-1,2,3,4-tetrahydronaphthalen-2-yl-acetyl)-L-thioproline (Compound 37)

mp: 170–180° C.
IR (KBr) cm$^{-1}$: 2925, 2550, 1710, 1600, 1450, 1430, 800, 720.
3-(5,7-Dimethyl-1,2,3,4-tetrahydronaphthalen-2-yl-acetyl)-L-thioproline ethyl ester (Compound 38)
IR (neat) cm$^{-1}$: 2900, 1735, 1650, 1400.
3-(5,7-Dimethyl-1,2,3,4-tetrahydronaphthalen-2-yl-acetyl)-L-thioproline (Compound 39)
IR (neat) cm$^{-1}$: 2900, 1730, 1610, 1420.
3-(2-Indanyl-acetyl)-D-thioproline (Compound 40)
mp: 111–113° C.
IR (KBr) cm$^{-1}$: 2800, 2550, 1720, 1600, 1460, 745.
1-[(S)-(−)-1,2,3,4-Tetrahydronaphthalen-2-yl-acetyl)-L-proline methyl ester (Compound 41)
mp: 62–64° C.
IR (KBr) cm$^{-1}$: 3070–2830, 1755, 1640, 1430, 1170, 750.
1-[(S)-(−)-1,2,3,4-Tetrahydronaphthalen-2-yl-acetyl)-L-proline (Compound 42)
mp: 129–130° C., $[\alpha]_D$–111.8° (C=1.00, MeOH)
IR (KBr) cm$^{-1}$: 3070–2470, 1730, 1590, 1450, 1175, 740.
1-[(R)-(+)-1,2,3,4-Tetrahydronaphthalen-2-yl-acetyl)-L-proline methyl ester (Compound 43)
$[\alpha]_D$–8.3° (C=1.07, MeOH)
IR (neat) cm$^{-1}$: 3060–2840, 1740, 1640, 1430, 1170, 745.
1-[(R)-(+)-1,2,3,4-Tetrahydronaphthalen-2-yl-acetyl)-L-proline (Compound 44)
mp: 153–154° C., $[\alpha]_D$–0.2° (C=0.95, MeOH)
IR (KBr) cm$^{-1}$: 3200–2500, 1750, 1610, 1450, 1195, 765.
3-[(S)-(−)-1,2,3,4-Tetrahydronaphthalen-2-yl-acetyl)-D-thioproline ethyl ester (Compound 45)
mp: 81–83° C., $[\alpha]_D$+39.7° (C=1.01, MeOH)
IR (KBr) cm$^{-1}$: 3000–2825, 1735, 1645, 1405.
3[(S)-(−)-1,2,3,4-Tetrahydronaphthalen-2-yl-acetyl)-D-thioproline (Compound 46)
mp: 145–149° C., $[\alpha]_D$+34.2° (C=0.93, MeOH)
IR (KBr) cm$^{-1}$: 3250–2300, 1705, 1600, 1420, 745.
3-[(R)-(+)-1,2,3,4-Tetrahydronaphthalen-2-yl-acetyl)-L-thioproline ethyl ester (Compound 47)
mp: 78–80° C., $[\alpha]_D$–41.7° (C=1.09, MeOH)
IR (KBr) cm$^{-1}$: 3050–2840, 1740, 1650, 1410, 750.
3-[(R)-(+)-1,2,3,4-Tetrahydronaphthalen-2-yl-acetyl)-L-thioproline (Compound 48)
mp: 151–152° C., $[\alpha]_D$–32.6° (C=0.68, MeOH)
IR (KBr) cm$^{-1}$: 2900, 2550, 1700, 1600, 1420, 740.
3-[3-(2-Indanyl-acetyl)-L-thioprolyl]thiazolidine (Compound 49)
IR (neat) cm$^{-1}$: 2925, 1640, 1405, 740.
1-[3-(2-Indanyl-acetyl)-L-thioprolyl]pyrrolidine (Compound 50)
mp: 82–83° C.
IR (KBr) cm$^{-1}$: 3070–2830, 1640, 1420, 750.
3-[1-(2-Indanylacetyl)-L-prolyl]thiazolidine (Compound 51)
IR (neat) cm$^{-1}$: 3070–2830, 1640, 1420, 1320, 1260, 1180, 740.
1-[1-(2-Indanylacetyl)-L-prolyl]pyrrolidine (compound 52)
IR (neat) cm$^{-1}$: 3080–2880, 1640, 1430, 1340, 1320, 745.
3-[4-(2-Indanylacetyl)-DL-1,4-thiazan-3-yl-carbonyl]-thiazolidine (Compound 53)
IR (neat) cm$^{-1}$: 2972, 1643, 1433, 1340, 1286, 1225, 1190.
1-[4-(2-Indanylacetyl)-DL-1,4-thiazan-3-yl-carbonyl]-pyrrolidine (Compound 54)
IR (neat) cm$^{-1}$: 2930, 1643, 1418, 1300, 1285, 1260, 1182, 1022.
3-[1-(2-Indanylacetyl)-DL-1,4-piperidin-2-yl-carbonyl]-thiazolidine (Compound 55)
IR (neat) cm$^{-1}$: 2925, 1630, 1420, 740.
1-[1-(2-Indanylacetyl)-DL-piperidin-2-yl-carbonyl]-pyrrolidine (Compound 56)
IR (neat) cm$^{-1}$: 2950, 2870, 1640, 1420, 750.
3-[1-(2-Indanylacetyl)-L-piperidin-2-yl-carbonyl]-thiazolidine (Compound 57)
IR (neat) cm$^{-1}$: 2910, 1630, 1410, 740.
1-[1-(2-Indanylacetyl)-L-piperidin-2-yl-carbonyl]-pyrrolidine (Compound 58)
IR (neat) cm$^{-1}$: 2940, 2850, 1620, 1420, 730.
1-[1-(2-Indanylacetyl)-D-piperidin-2-yl-carbonyl]-pyrrolidine (Compound 59)
IR (neat) cm$^{-1}$: 2930, 2850, 1630, 1420, 730.
3-[1-(1,2,3,4-Tetrahydronaphthalen-2-yl-carbonyl)-L-prolyl]thiazolidine (Compound 60)
IR (neat) cm$^{-1}$: 3070–2880, 1650, 1430, 1360, 1340, 1325, 750.
1-[1-(1,2,3,4-Tetrahydronaphthalen-2-yl-carbonyl)-L-prolyl]-pyrrolidine (Compound 61)
IR (neat) cm$^{-1}$: 3070–2880, 1640, 1435, 1360, 1340, 750.
3-[1-(1,2,3,4-Tetrahydronaphthalen-2-yl-acetyl)-L-prolyl]-thiazolidine (Compound 62)
IR (neat) cm$^{-1}$: 2920, 1630, 1420, 740.
3-[3-(2-Indanylacetyl)-L-thioprolyl]-L-thioproline ethyl ester (Compound 63)
IR (neat) cm$^{-1}$: 2940, 1740, 1650, 1400, 740.
1-[1-(2-Indanylacetyl)-L-prolyl]-L-proline methyl ester (Compound 64)
IR (neat) cm$^{-1}$: 2950, 1740, 1630, 1430, 740.
1-[1-(2-Indanylacetyl)-L-prolyl]-L-proline (Compound 65)
mp: 163–165° C.
IR (KBr) cm$^{-1}$: 2950, 1720, 1655, 1600, 1430, 740.
1-[1-(2-Indanylacetyl)-L-prolyl]-L-prolinol (Compound 66)
IR (neat) cm$^{-1}$: 3410, 2970–2850, 1635, 1440, 745.
1-[1-(2-Indanyiacetyl)-L-prolyl]-L-prolinal (Compound 67)
IR (neat) cm$^{-1}$: 3070–2850, 1735, 1640, 1435, 750.
3-[3-(1,2,3,4-Tetrahydronaphthalen-2-yl-acetyl)-L-thioprolyl]thiazolidine (Compound 68)
mp: 80–96° C.
IR (KBr) cm$^{-1}$: 2920, 1635, 1430, 1400, 750.
1-[3-(1,2,3,4-Tetrahydronaphthalen-2-yl-acetyl)-L-thioprolyl]pyrrolidine (Compound 69)
mp: 118–129° C.
IR (KBr) cm$^{-1}$: 2920, 1635, 1435, 1400, 745.
1-[1-(1,2,3,4-Tetrahydronaphthalen-2-yl-acetyl)-L-prolyl]-pyrrolidine (Compound 70)
mp: 110–113° C.
IR (KBr) cm$^{-1}$: 3070–2850, 1635, 1440, 1420, 1320, 750.

Synthetic Example 71

1-[3-[3-Indan-2-yl)propionyl]-L-thioprolyl]pyrrolidine (Compound 71)

Suspended in 20 ml of methylene chloride was 0.89 g of 1-L-thioprolylpyrrolidine hydrochloride, and 0.40 g of triethylamine and 0.76 g of 3-(indan-2-yl)propionic acid were added while chilling with ice water and stirring. After the mixture was chilled with ice water and stirred for 10 minutes, 0.92 g of WSC.HCL was added while chilling with ice water and stirring, followed by further stirring at room temperature for 16 hours. The resultant liquid reaction mixture was washed with diluted hydrochloric acid, water and an aqueous solution of sodium bicarbonate in that order. After an organic layer was dried over anhydrous magnesium sulfate, the solvent was distilled off under reduced pressure, and the resultant residue was subjected to recrystallization from a mixed solvent of ethyl acetate-isopropyl ether, thereby obtaining 1.02 g (71%) of 1-[3-[3-indan-2-yl) propionyl]-L-thioprolyl]pyrrolidine as colorless crystals.

mp: 92–937° C.
IR (KBr) cm$^{-1}$: 2900, 1660, 1640, 1410, 750.

Synthetic Examples 72–130

The following compounds were synthesized in the same manner as in Synthetic Example 71.

1-[3-[4-Indan-2-yl)butanoyl]-L-thioprolyl]pyrrolidine (Compound 72)
mp: 99–100° C.
IR (KBr) cm$^{-1}$: 2950, 1660, 1640, 1410, 750.

1-[3-(5-Chloroindan-2-yl-acetyl)-L-thioprolyl]pyrrolidine (Compound 73)
IR (neat) cm$^{-1}$: 2950, 1640, 1420, 750.

1-[3-(5-Methylindan-2-yl-acetyl)-L-thioprolyl]pyrrolidine (Compound 74)
mp: 115–123° C.
IR (KBr) cm$^{-1}$: 2970, 1630, 1440, 1410, 805, 780.

1-[3-(5-Nitroindan-2-yl-acetyl)-L-thioprolyl]pyrrolidine (Compound 75)
IR (neat) cm$^{-1}$: 2960, 1655, 1630, 1410, 735.

1-[3-(5-Aminoindan-2-yl-acetyl)-L-thioprolyl]pyrrolidine (Compound 76)
IR (neat) cm$^{-1}$: 3345, 2925, 1640, 1410, 750.

1-[3-(2-Indanylacetyl)-D-thioprolyl]pyrrolidine (Compound 77)
mp: 81–83° C.
IR (KBr) cm$^{-1}$: 2950, 1640, 1420, 750.

1-[1-(6-Methoxy-1,2,3,4-tetrahydronaphthalen-2-yl-acetyl)-L-prolyl]pyrrolidine (Compound 78)
IR (neat) cm$^{-1}$: 3050–2825, 1655, 1635, 1430, 1035.

1-[1-(6-Methoxy-1,2,3,4-tetrahydronaphthalen-2-yl-acetyl)-L-prolyl]thiazolidine (Compound 79)
IR (neat) cm$^{-1}$: 2910–2825, 1635, 1420, 1150.

1-[3-(6-Methoxy-1,2,3,4-tetrahydronaphthalen-2-yl-acetyl)-L-thioprolyl]pyrrolidine (Compound 80)
IR (neat) cm$^{-1}$: 2920, 1660, 1500, 1420, 750.

3-[3-(6-Methoxy-1,2,3,4-tetrahydronaphthalen-2-yl-acetyl)-L-thioprolyl]thiazolidine (Compound 81)
IR (neat) cm$^{-1}$: 2925, 1640, 1500, 1420, 750.

1-[3-(5,7-Dimethyl-1,2,3,4-tetrahydronaphthalen-2-yl-acetyl)-L-thioprolyl]pyrrolidine (Compound 82)
IR (neat) cm$^{-1}$: 2960–2860, 1640, 1410, 745.

1-[1-[(S)-(−)-1,2,3,4-Tetrahydronaphthalen-2-yl-acetyl)-L-prolyl]pyrrolidine (Compound 83)
mp: 104–106° C., $[\alpha]_D$−83.8° (C=1.0, MeOH)
IR (KBr) cm$^{-1}$: 3070–2830, 1650, 1635, 1435, 1425, 750.

1-[1-[(R)-(+)-1,2,3,4-Tetrahydronaphthalen-2-yl-acetyl]-L-prolyl]pyrrolidine (Compound 84)
mp: 109–110° C., $[\alpha]_D$+13.7° (C=1.0, MeOH)
IR (KBr) cm$^{-1}$: 2990–2830, 1630, 1440, 1415, 750.

3-[1-[(S)-(−)-1,2,3,4-Tetrahydronaphthalen-2-yl-acetyl]-L-prolyl]thiazolidine (Compound 85)
$[\alpha]_D$−69.5° (C=1.01, MeOH)
IR (neat) cm$^{-1}$: 2910, 1640, 1420, 745.

3-[1-[(R)-(+)-1,2,3,4-Tetrahydronaphthalen-2-yl-acetyl]-L-prolyl]thiazolidine (Compound 86)
mp: 97–99° C., $[\alpha]_D$+19.5° (C=0.67, MeOH)
IR (KBr) cm$^{-1}$: 3000–2840, 1625, 1450, 1420.

1-[3-[(S)-(−)-1,2,3,4-Tetrahydronaphthalen-2-yl-acetyl]-L-thioprolyl]pyrrolidine (Compound 87)
mp: 121–123° C., $[\alpha]_D$−153.1° (C=0.60, MeOH)
IR (KBr) cm$^{-1}$: 3050–2085, 1620, 1445, 1410.

1-[3-[(S)-(−)-1,2,3,4-Tetrahydronaphthalen-2-yl-acetyl]-D-thioprolyl]pyrrolidine (Compound 88)
mp: 153–155° C., $[\alpha]_D$+53.3° (C=1.01, MeOH)
IR (KBr) cm$^{-1}$: 3000–2840, 1635, 1440, 1400, 750.

1-[3-[(R)-(+)-1,2,3,4-Tetrahydronaphthalen-2-yl-thioprolyl]pyrrolidine (Compound 89)
mp: 154–156° C., $[\alpha]_D$−52.3° (C=0.85, MeOH)
IR (KBr) cm$^{-1}$: 2920, 1640, 1440, 1400, 750.

1-[3-[(R)-(+)-1,2,3,4-Tetrahydronaphthalen-2-yl-acetyl]-D-thioprolyl]pyrrolidine (Compound 90)
mp: 121–123° C., $[\alpha]_D$+149.9° (C=0.72, MeOH)
IR (KBr) cm$^{-1}$: 3050–2825, 1630, 1445, 1410, 750.

3-[3-[(S)-(−)-1,2,3,4-Tetrahydronaphthalen-2-yl-acetyl]-L-thioprolyl]thiazolidine (Compound 91)
mp: 119–121° C., $[\alpha]_D$−128.6° (C=0.73, MeOH)
IR (KBr) cm$^{-1}$: 3050–2825, 1640, 1620, 1410, 745.

3-[3-[(R)-(+)-1,2,3,4-Tetrahydronaphthalen-2-yl-acetyl]-L-thioprolyl]thiazolidine (Compound 92)
mp: 152–154° C., $[\alpha]_D$−35.7° (C=0.23, MeOH)
IR (KBr) cm$^{-1}$: 2910, 1630, 1430, 1405, 750.

3-(1-Oxoindan-2-yl-acetyl)-L-thioproline ethyl ester (Compound 93)
IR (neat) cm$^{-1}$: 2945, 1740, 1705, 1660, 1610, 1465, 1410, 1295, 1200, 1025, 750.

3-(1-Oxoindan-2-yl-acetyl)-L-thioproline (Compound 94)
mp: 108–111° C.
IR (KBr) cm$^{-1}$: 3450, 2945, 1710, 1650, 1610, 1415, 1300, 1210, 745.

3-[3-(1-Oxoindan-2-yl-acetyl)-L-thioprolyl]thiazolidine (Compound 95)
mp: 80–88° C.
IR (KBr) cm$^{-1}$: 3000–2930, 1705, 1650, 1420, 750.

1-[3-(1-Oxoindan-2-yl-acetyl)-L-thioprolyl(pyrrolidine (Compound 96)
mp: 131–139° C.
IR (KBr) cm$^{-1}$: 2980, 2890, 1710, 1640, 1425, 1290, 1170, 750.

1-(Indan-2-yl-acetyl)-L-prolinol (Compound 97)
mp: 74–75° C.
IR (KBr) cm$^{-1}$: 3600–3200, 3000–2800, 1620, 1480–1400, 1060.

3-(Indan-2-yl-acetyl)-L-thioprolinol (Compound 98)
mp: 76–78° C.
IR (KBr) cm$^{-1}$: 3420, 3080–2850, 1630, 1430, 1060, 750.

1-((R,S)-1,2,3,4-Tetrahydronaphthalen-2-yl-acetyl]-L-prolinol (Compound 99)
IR (neat) cm$^{-1}$: 3350, 2900, 1610, 1445, 1430, 1045.

1-((R,S)-5,7-Dimethyl-1,2,3,4-tetrahydronaphthalen-2-yl-acetyl]-L-prolinol (Compound 100)
mp: 93–940° C.
IR (KBr) cm$^{-1}$: 3370, 2920, 1630, 1610, 1440, 1060.

1-(Indan-2-yl-carbonyl)-L-prolinol (Compound 101)
mp: 100–101° C.
IR (KBr) cm$^{-1}$: 3380, 1620, 1420, 1050, 750.

1-((R,S)-5-Methylindan-2-yl-acetyl)-L-prolinol (Compound 102)
IR (neat) cm$^{-1}$: 3400, 2910, 1610, 1430, 1050, 810.

1-((R,S)-5-Methoxyindan-2-yl-acetyl)-L-prolinol (Compound 103)
IR (neat) cm$^{-1}$: 3600–3200, 3000–2800, 1610, 1485, 1430, 1010, 800.

1-((R,S)-7-Methoxy-1,2,3,4-tetrahydronaphthalen-2-yl-acetyl]-L-prolinol (Compound 104)
mp: 86–88° C.
IR (KBr) cm$^{-1}$: 3350, 3000–2800, 1610, 1500, 1436, 1050, 720.

1-((R,S)-5-Nitroindan-2-yl-acetyl)-L-prolinol (Compound 105)
IR (neat) cm$^{-1}$: 3600–3000, 2950–2800, 1605, 1510, 1430, 1340, 805, 740.

1-[4-(Indan-2-yl)butanoyl]-L-prolinol (Compound 106)
IR (neat) cm$^{-1}$: 3380, 2920, 1615, 1430, 740.

1-((S)-1,2,3,4-Tetrahydronaphthalen-2-yl-acetyl]-L-prolinol (Compound 107)

mp: 70–71° C.
IR (KBr) cm$^{-1}$: 3230, 2920, 1605, 1435, 750.

1-((R,S)-5-Aminoindan-2-yl-acetyl)-L-prolinol (Compound 108)
mp: 93–95° C.
IR (KBr) cm$^{-1}$: 3340, 2930, 1625, 1430, 1140.

1-((R,S)-5-Chloroindan-2-yl-acetyl)-L-prolinol (Compound 109)
IR (neat) cm$^{-1}$: 3600–3200, 2900–2800, 1610, 1430, 1050, 880, 805.

1-(Indan-2-yl-acetyl)-D-prolinol (Compound 110)
mp: 75–76° C.
IR (KBr) cm$^{-1}$: 3360, 1620, 1440, 1050, 745.

1-[3-(Indan-2-yl-acetyl)-L-thioprolyl]-L-prolinol (Compound 111)
IR (neat) cm$^{-1}$: 3400, 3000–2800, 1640, 1420, 740.

1-[3-(Indan-2-yl-acetyl)-L-thioprolyl]-L-prolinal (Compound 112)
IR (neat) cm$^{-1}$: 3400, 3100–2800, 1730, 1640, 1420, 750.

3-[1-(Indan-2-yl-acetyl)-L-prolyl]-L-thioprolinol (Compound 113)
IR (KBr) cm$^{-1}$: 3360, 2900, 1630, 1420, 750.

1-[3-((S)-1,2,3,4-Tetrahydronaphthalen-2-yl-acetyl)-L-thioprolyl]-L-prolinol (Compound 114)
IR (KBr) cm$^{-1}$: 3400, 2910, 1625, 1410, 740.

3-[3-((S)-1,2,3,4-Tetrahydronaphthalen-2-yl-acetyl)-L-thioprolyl]-L-thioprolinol (Compound 115)
IR (KBr) cm$^{-1}$: 3400, 2910, 1630, 1410, 740.

3-[1-(Indan-2-yl-acetyl)-L-prolyl]-L-thioprolinal (Compound 116)
IR (neat) cm$^{-1}$: 3350, 2900–2800, 1725, 1610, 1420, 740.

1-[3-((S)-1,2,3,4-Tetrahydronaphthalen-2-yl-acetyl)-L-thioprolyl]-L-prolinal (Compound 117)
IR (KBr) cm$^{-1}$: 3430, 2920, 1725, 1635, 1410, 745.

3-[3-((S)-1,2,3,4-Tetrahydronaphthalen-2-yl-acetyl)-L-thioprolyl]-L-thioprolinal (Compound 118)
IR (KBr) cm$^{-1}$: 3430, 2920, 1730, 1635, 1410, 745.

(2S)-1-[1-((S)-1,2,3,4-Tetrahydronaphthalen-2-yl-acetyl)-L-prolyl]-2-pyrrolidine carbaldehyde dimethyl acetal (Compound 119)
mp: 103–106° C.
IR (KBr) cm$^{-1}$: 3600–3200, 3000–2800, 1630, 1420, 750.

1-[3-(Indan-2-yl-acetyl)-L-thioprolyl]-L-prolinol (Compound 120)
IR (neat) cm$^{-1}$: 3600–3100, 3000–2800, 1630, 1410, 740.

3-[1-(Indan-2-yl-acetyl)-L-prolyl]-L-thioprolinol (Compound 121)
IR (neat) cm$^{-1}$: 3600–3100, 3000–2800, 1630, 1410, 740.

1-[3-((S)-1,2,3,4-Tetrahydronaphthalen-2-yl-acetyl)-L-thioprolyl]-L-prolinol (Compound 122)
IR (neat) cm$^{-1}$: 3600–3100, 3000–2800, 1620, 1420, 740.

(2S)-1-[3-(Indan-2-yl-acetyl)-L-thioprolyl]-2-cyano-pyrrolidine (Compound 123)
mp: 99–100° C.
IR (KBr) cm$^{-1}$: 3600–3200, 3000–2800, 2230, 1655, 1405.

(2S)-1-[1-(Indan-2-yl-acetyl)-L-prolyl]-2-cyanopyridine (Compound 124)
IR (neat) cm$^{-1}$: 3600–3200, 3000–2800, 1630, 1420, 740.

(2S)-1-[1-((S)-1,2,3,4-Tetrahydronaphthalen-2-yl-acetyl)-L-prolyl]-2-cyanopyrrolidine (Compound 125)
mp: 100–101° C.
IR (KBr) cm$^{-1}$: 3600–3300, 3000–2800, 2300, 1660, 1625, 1410.

(2S)-1-[3-((S)-1,2,3,4-Tetrahydronaphthalen-2-yl-acetyl)-L-thioprolyl]-2-cyanopyrrolidine (Compound 126)
IR (neat) cm$^{-1}$: 3650–3100, 3000–2800, 1625, 1410, 740.

1-[3-(Indan-2-yl-acetyl)-L-thioprolyl]-L-prolinal (Compound 128)
IR (KBr) cm$^{-1}$: 3650–3100, 3000–2800, 1730, 1640, 1410, 740.

3-[1-(Indan-2-yl-acetyl)-L-prolyl]-L-thioprolinal (Compound 129)
IR (KBr) cm$^{-1}$: 3650–3100, 3000–2800, 1730, 1630, 1410, 740.

1-[3-((S)-1,2,3,4-Tetrahydronaphthalen-2-yl-acetyl)-L-thioprolyl]-L-prolinal (Compound 130)
mp: 103–104° C.
IR (KBr) cm$^{-1}$: 3000–2800, 1725, 1640, 1410, 740.

Synthetic Example 131

3-(2-Indanacetyl)-4(R)-(1-pyrrolidinecarbonyl)thiazolidine 1-oxide (Compound 131)

Dissolved in 100 ml of chloroform were 5 g of 3-(2-indanacetyl)-4(R)-(1-pyrrolidinecarbonyl)thiazolidine (a compound according to Preparation Example 2 set forth in Japanese Patent Application Laid-Open No. 262557/1990). While chilling with ice water, 3.3 g of meta-chloroperbenzoic acid were gradually added to the solution. After stirring the mixture for 3 hours, the resultant liquid reaction mixture was washed successively with a 5% solution of sodium thiosulfate and a saturated aqueous solution of sodium bicarbonate and dried over anhydrous magnesium sulfate. The solvent was distilled off under reduced pressure, and the residue was purified by column chromatography on silica gel (methanol:chloroform=5:95), thereby obtaining 3.8 g of the title compound as a diastereomeric mixture. Yield: 73%.

The diastereomeric mixture thus obtained was resolved into the individual isomers by high-performance liquid chromatography (Inertsil ODS column, water:acetonitrile =3:2). After the solvent was distilled out of the individual isomers, the resultant crystals were separately recrystallized from a mixed solvent of ethyl acetate-isopropyl ether, thereby obtaining Isomer A and Isomer B.

Isomer A
mp: 123° C., $[\alpha]_D^{25}$ –85° (C=0.9, MeOH)
IR (KBr) cm$^{-1}$: 1645.

Isomer B
mp: 120° C., $[\alpha]_D^{25}$ –69° (C=1.0, MeOH)
IR (KBr) cm$^{-1}$: 1660, 1640.

Synthetic Example 132

3-(2-Indanacetyl)-4(R)-(1-pyrrolidinecarbonyl)thiazolidine 1,1-dioxide (Compound 132)

Dissolved in 100 ml of chloroform were 5 g of 3-(2-indanacetyl)-4(R)-(1-pyrrolidinecarbonyl)thiazolidine (a compound according to Preparation Example 2 set forth in Japanese Patent Application Laid-Open No. 262557/1990). While chilling with ice water, 6.7 g of meta-chloroperbenzoic acid were gradually added to the solution. After stirring the mixture at room temperature for 3 hours, the resultant liquid reaction mixture was washed successively with a 5% solution of sodium thiosulfate and a saturated aqueous solution of sodium bicarbonate and dried over anhydrous magnesium sulfate. The solvent was distilled off under reduced pressure, and the residue was purified by column chromatography on silica gel (methanol:chloroform =5:95). The resultant crystals were recrystallized from a mixed solvent of ethyl acetate-isopropyl ether, thereby obtaining 3.4 g of the title compound. Yield: 62%.

mp: 132–1330° C., $[\alpha]_D^{22}$ –35° (C=1.0, MeOH)
IR (KBr) cm$^{-1}$: 1667, 1642.

Synthetic Examples 133 and 134

The following compounds were synthesized in the same manner as in Example 132.

3-(2-(S)-1,2,3,4-Tetrahydronaphthaleneacetyl)-4(R)-(1-pyrrolidinecarbonyl)thiazolidine 1-oxide (Compound 133)

IR (neat) cm$^{-1}$: 1650.

3-(2-(S)-1,2,3,4-Tetrahydronaphthaleneacetyl)-4(R)-(1-pyrrolidinecarbonyl)thiazolidine 1,1-dioxide (Compound 134)

IR (KBr) cm$^{-1}$: 1655.

Synthetic Example 135

3-(1-Hydroxy-2-indanacetyl)-4-(R)-(1-pyrrolidinecarbonyl)thiazolidine 1-oxide (Compound 135)

Dissolved in 20 ml of methanol were 500 mg of 3-(1-oxo-2-indanacetyl)-4-(R)-(1-pyrrolidinecarbonyl)thiazolidine, and 80 mg of NaBH$_4$ were added to the solution. After stirring the mixture at room temperature, the resultant liquid reaction mixture was concentrated under reduced pressure, and the residue was added with water and extracted with chloroform. After the extract was dried over anhydrous magnesium sulfate, chloroform was distilled off under reduced pressure to obtain 545 mg of 3-(1-hydroxy-2-indanacetyl)-4-(R)-(1-pyrrolidinecarbonyl)thiazolidine. Thereafter, the process was allowed to progress in accordance with the process of Synthetic Example 1, thereby obtaining the title compound as a diastereomeric mixture. Yield: 87% (amorphous).

IR (KBr) cm$^{-1}$: 3400, 1640.

Preparation Example 1

Fifty grams of Compound 1 were uniformly mixed with 315 g of lactose, 125 g of corn starch and 25 g of crystalline cellulose, and 200 ml of a 7.5% aqueous solution of hydroxypropylcellulose were added to the mixture. The mixture was extruded into granules through an extrusion granulator making use of a screen having openings of 0.5 mm in diameter. The granules were immediately rounded by a Marumelyzer and then dried, thereby obtaining a granular preparation.

Preparation Example 2

The dry granular preparation obtained in Preparation Example 1 was coated with 1.9 kg of a film coating liquid having the following composition by means of a fluidized-bed granulator, thereby obtaining an enteric coated granular preparation.

Composition of coating liquid

| Hydroxypropylmethylcellulose phthalate | 5.0 wt. % |
|---|---|
| Stearic acid | 0.25 wt. % |
| Methylene chloride | 50.0 wt. % |
| Ethanol | 44.75 wt. %. |

Preparation Example 3

Twenty grams of Compound 18 were uniformly mixed with 100 g of lactose, 36 g of corn starch, 30 g of crystalline cellulose, 10 g of calcium carboxymethylcellulose and 4 g of magnesium stearate. The mixture was tableted by a single tablet machine with a pestle 7.5 mm in diameter, thereby obtaining a tablet preparation having a weight of 200 mg/tablet.

Preparation Example 4

The tablet preparation obtained in Preparation Example 3 was coated with a coating liquid having the following composition by spray coating so as to apply a coating at a rate of 10 mg/tablet, thereby obtaining an enteric coated tablet preparation.

Composition of coating liquid

| Hydroxypropylmethylcellulose phthalate | 8.0 wt. % |
|---|---|
| Glycerol fatty acid ester | 0.4 wt. % |
| Methylene chloride | 50.0 wt. % |
| Bleached beeswax | 0.1 wt. % |
| Isopropanol | 41.5 wt. % |

EXAMPLE 1

<Cholinesterase-activating effect by single administration>

1-[3-(2-Indanylacetyl)-L-thioprolyl]pyrrolidine (Compound 50) was orally administered at a dose of 100 mg/kg to male Fischer rats. Two days after the administration, blood was collected from each rat to obtain a serum. Serum cholinesterase activities were measured by using acetylthiocholine as a substrate according to the method of Ellman et al.

As a result, supposing that cholinesterase activities after a vehicle (a 10% solution of gum arabic) was administered as a control were 100%, cholinesterase activities after the administration of Compound 50 amounted to 145%. Incidentally, the other compounds (I) were tested in the same manner as described above. As a result, cholinesterase activities after the administration of the compounds (I) amounted to 140–300%.

EXAMPLE 2

<Cholinesterase-activating effect by repeated administration-1>

1-[3-(1,2,3,4-Tetrahydronaphthalen-2-yl-acetyl)-L-thioprolyl]pyrrolidine (Compound 69) was orally administered at a dose of 30 mg/kg once a day for 28 days to male Fischer rats. Two days after the final administration, blood was collected from each rat to obtain a serum. Serum cholinesterase activities were measured by using butyrylthiocholine as a substrate according to the method of Ellman et al.

As a result, supposing that cholinesterase activities after a vehicle (a 10% solution of gum arabic) was administered as a control were 100%, cholinesterase activities after the administration of Compound 69 amounted to 213%. Incidentally, the other compounds (I) were tested in the same manner as described above. As a result, cholinesterase activities after the administration of the compounds (I) amounted to 150–250%.

EXAMPLE 3

<Cholinesterase-activating effect by repeated administration-2>

1-[3-(2-Indanylacetyl)-L-thioprolyl]pyrrolidine (Compound 50) or N-benzyloxycarbonyl-prolylprolinal (Compound 7) was orally administered at a dose of 3×10$^{-5}$ mol/kg once a day for 7 days to male Fischer rats. Two days after the final administration, blood was collected from each rat to obtain a serum. Serum cholinesterase activities were measured by using acetylthiocholine as a substrate according to the method of Ellman et al.

As a result, supposing that cholinesterase activities after a vehicle (a 10% solution of gum arabic) was administered as a control were 100%, cholinesterase activities after the administration of Compound 50 or Compound 7 amounted to 143%. Incidentally, the other compounds (I) were tested in the same manner as described above. As a result, cholinesterase activities after the administration of the compounds (I) amounted to 140–200%.

Further, even when the above test compounds were administered at doses of 100 mg/kg and 1,000 mg/kg in the same manner as described above, cholinesterase activities in brain parenchyma were observed undergoing no change compared with the control group.

EXAMPLE 4

<Combined experiment with THA—sialorrhea>

1-[3-(2-Indanylacetyl)-L-thioprolyl]pyrrolidine (Compound 50) was orally administered at a dose of 1,000 mg/kg to male ICR mice. After 2 days, THA was orally administered at a dose of 40 mg/kg, and the degree of sialorrhea was scored at 60 minutes after the administration of THA. The score was ranked as 0 where no sialorrhea was manifested, 1 where sialorrhea was slightly manifested, 2 where sialorrhea was moderately manifested, or 3 where sialorrhea was seriously manifested.

As a result, no sialorrhea was observed on the groups to which the control solvent and Compound 50 were respectively administered, but sialorrhea was observed with the score of 1.5 in the group to which THA was administered. However, sialorrhea was mitigated to the score of 0.5 in the group to which Compound 50 and THA were administered in combination. Incidentally, the other compounds (I) were tested in the same manner as described above. As a result, the score of the group, to which THA was administered, was 1.5–2.5, while the score of the group, to which each of the compounds (1) and THA were administered in combination, was 0–1.0.

EXAMPLE 5

<Combined experiment with THA—hepatopathy>

1-[3-(2-Indanylacetyl)-L-thioprolyl]pyrrolidine (Compound 50) was orally administered at a dose of 1,000 mg/kg to male ICR mice. After 2 days, THA was orally administered at a dose of 40 mg/kg. Upon elapsed time of 24 hours after the administration of THA, blood was collected from an abdominal aorta of each mouse under ether anesthesia to obtain a serum. The measurement of GOT activities was performed by the ultraviolet absorption method according to the method of Karmen.

Serum GOT activities were raised to 270% in comparison with the control group, to which the solvent was administered, by the administration of THA, while the group, to which Compound 50 and THA were administered in combination, showed serum GOT activities of 138% in comparison with the control group to which the solvent was administered. This indicates that hepatopathy was mitigated by the combined use of the compound (I). Incidentally, the other compounds (I) were tested in the same manner as described above. As a result, the serum GOT activities of the THA-administered group were 200–300%, while the GOT activities of the group, to which each of the compounds (1) and THA were administered in combination, were 100–150%.

EXAMPLE 6

<Toxicity test>

Five male ICR mice aged 4–5 weeks were used in each group. 1-[3-(2-Indanylacetyl)-L-thioprolyl]pyrrolidine (Compound 50) was orally administered at a dose of 1,500 mg/kg to the mice to observe them over 7 days.

As a result, the mice underwent no change in general symptom under the above conditions, and no lethal case was observed.

Industrial Applicability

The cholinesterase activators according to the present invention have a strongly activating action on cholinesterase, in particular, a selectively activating action on peripheral cholinesterase and are also high in safety. They are hence useful as agents for preventing and treating the side effects of central cholinesterase inhibitors, in particular, hepatopathy, and agents for preventing and treating the side effects of various medicines manifested on the basis of a cholinesterase-inhibiting action.

We claim:

1. A method for preventing or treating a disease, wherein the disease is manifested by a reduction in a cholinesterase activity, wherein the method comprises the step of administering to a patient in need thereof an effective amount of a cholinesterase activator containing a compound represented by the formula:

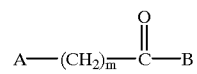

wherein A is a group represented by the following formula:

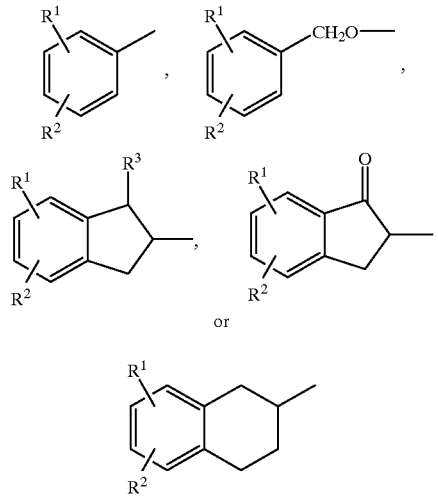

wherein $R^1$ and $R^2$ are identical with or different from each other and denote individually a hydrogen atom, alkyl group, alkoxyl group, nitro group, amino group or halogen atom; $R^3$ is a hydrogen atom or a hydroxyl group; and B is a group represented by the following formula:

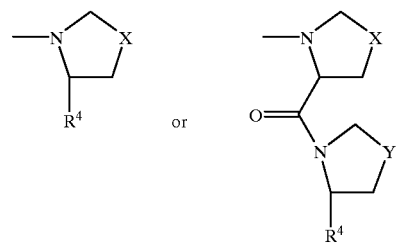

wherein $R^4$ is a hydrogen atom, formyl group, cyano group, dialkoxymethyl group, carboxyl group, alkoxycarbonyl group or hydroxymethyl group; X is a methylene group, ethylene group, oxygen atom, sulfur atom, sulfinyl group, sulfonyl group or —$CH_2$—S—; Y is a methylene group, ethylene group, —$CH_2$—S—, sulfur atom, sulfinyl group or sulfonyl group; and m is an integer of 0 to 5.

2. The method of claim 1, wherein the cholinesterase activator activates a peripheral cholinesterase.

3. A method for activating a cholinesterase comprising the step of contacting the cholinesterase with a compound represented by the formula:

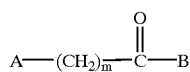

wherein A is a group represented by the following formula:

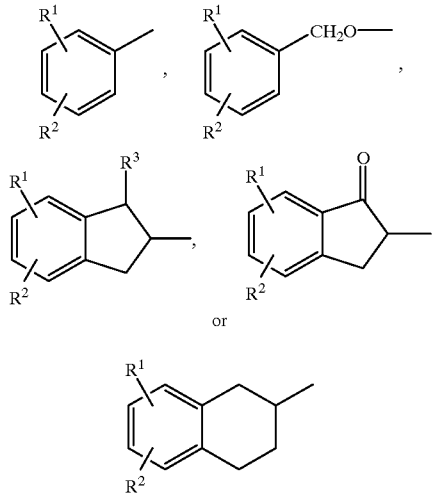

wherein $R^1$ and $R^2$ are identical with or different from each other and denote individually a hydrogen atom, alkyl group, alkoxyl group, nitro group, amino group or halogen atom; $R^3$ is a hydrogen atom or a hydroxyl group; and B is a group represented by the following formula:

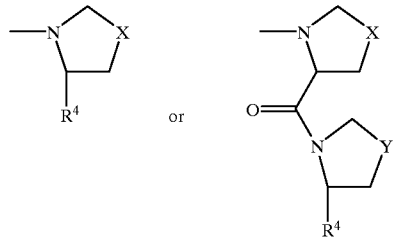

wherein $R^4$ is a hydrogen atom, formyl group, cyano group, dialkoxymethyl group, carboxyl group, alkoxycarbonyl group or hydroxymethyl group; X is a methylene group, ethylene group, oxygen atom, sulfur atom, sulfinyl group, sulfonyl group or —$CH_2$—S—; Y is a methylene group, ethylene group, —$CH_2$—S—, sulfur atom, sulfinyl group or sulfonyl group; and m is an integer of 0 to 5.

4. The method of claim 3, wherein the cholinesterase is a peripheral cholinesterase.

* * * * *